United States Patent [19]

Wriede et al.

[11] Patent Number: 5,076,829
[45] Date of Patent: Dec. 31, 1991

[54] SUBSTITUTED 2,3-EPOXY-5-CYCLOHEXENONE DERIVATIVES, AND FUNGICIDES AND HERBICIDES CONTAINING SAME

[75] Inventors: Ulrich Wriede, Limburgerhof; John-Bryan Speakman, Mannheim; Rudolf Karl; Ernst-Heinrich Pommer, both of Limburgerhof; Eberhard Ammermann, Ludwigshafen; Bruno Wuerzer, Otterstadt, all of Fed. Rep. of Germany

[73] Assignee: BASF Aktiengesellschaft, Ludwigshafen, Fed. Rep. of Germany

[21] Appl. No.: 512,509

[22] Filed: Apr. 20, 1990

Related U.S. Application Data

[63] Continuation of Ser. No. 158,762, Feb. 22, 1988, abandoned.

[30] Foreign Application Priority Data

Mar. 7, 1987 [DE] Fed. Rep. of Germany ....... 3707358

[51] Int. Cl.$^5$ .................. A01N 43/20; A61K 31/34; C07D 305/06
[52] U.S. Cl. .................................. 71/88; 549/546; 514/475
[58] Field of Search ................... 71/82; 549/546; 514/475

[56] References Cited

U.S. PATENT DOCUMENTS 3,701,790 10/1972 Coats et al. ............. 549/546

FOREIGN PATENT DOCUMENTS 113107 7/1983 Japan ...................... 71/88
174304 10/1983 Japan .

OTHER PUBLICATIONS

Blazejewski, et al., *J. Chem. Soc. Perkin Trans 1.*, p. 1861, Compound 9 (1987), "Chlorous Acid Oxidation of Trifluoromethylphenols".
Hayoshi et al., *Agr. Biol. Chem.*, vol. 43, p. 114, Compound 6 (1979), "Methoxy-1,4-benzoquinone and Methyl Gallate, Inhibitory Factors of Betacyanin Synthesis . . . ".
*Chem Abstract*, vol. 100: 63508a, (1984), "Quinone Derivatives as Herbicides".
Alder et al., *Chem. Ber.*, vol. 93, No. 8, (1960), "Darstellung von p-Chinon-epoxyden".
Ichihara et al., *Agr. Chem.*, vol. 39, p. 555, Compound 7, (1975), "Synthesis of 7-Desoxypanepoxydol".

*Primary Examiner*—Richard L. Raymond
*Assistant Examiner*—Mark W. Russell
*Attorney, Agent, or Firm*—Oblon, Spivak, McClelland, Maier & Neustadt

[57] ABSTRACT

2-substituted 2,3-epoxy-5-cyclohexenone derivatives of the formula I

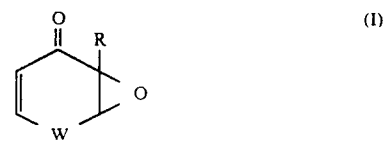

where W is C=O or CHOR$^1$, R$^1$ is hydrogen, alkyl, alkenyl, alkynyl or alkoxycarbonyl, R is a substituted or unsubstituted hydrocarbon chain, or phenyl or phenylalkyl whose phenyl radical is substituted or unsubstituted and whose alkyl radical may be interrupted by O or S and fungicides and herbicides containing these compounds.

7 Claims, No Drawings

SUBSTITUTED 2,3-EPOXY-5-CYCLOHEXENONE DERIVATIVES, AND FUNGICIDES AND HERBICIDES CONTAINING SAME

This application is a continuation of application Ser. No. 07/158,762, filed on Feb. 22, 1988, now abandoned.

The present invention relates to novel 2-substituted 2,3-epoxy-5-cyclohexenone derivatives, processes for their preparation, and their use as fungicides and herbicides.

It is known that N-trichloromethylthiotetrahydrophthalimide can be used as a fungicide (Wegler, Chemie der Pflanzenschutz- und Schädlingsbekämpfungsmittel, 2 (1970), 109).

The compound 2-hydroxmethyl-2,3-epoxy-5-cyclohexene-1,4-dione is also known (Japanese Laid-Open Application 83/174,304).

We have found that novel 2-substituted 2,3-epoxy-5-cyclohexenone derivatives of the formula I

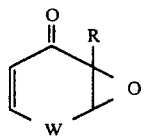

where W is C=O or CHOR$^1$, R$^1$ is hydrogen, C$_1$–C$_4$-alkyl, C$_2$–C$_4$-alkenyl, C$_2$–C$_4$-alkynyl or C$_2$–C$_4$-alkylcarbonyl, R is a straight-chain or branched, saturated or unsaturated hydrocarbon radical of 1 to 10 carbon atoms which is unsubstituted or substituted by halogen, or is the radical

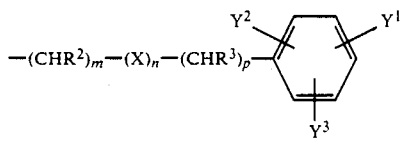

where R$^2$ and R$^3$ independently of one another are each hydrogen or methyl, X is oxygen or sulfur, Y$^1$, Y$^2$ and Y$^3$ are each hydrogen, C$_1$–C$_4$-alkyl, C$_1$–C$_4$-alkoxy, C$_1$–C$_4$-haloalkyl, C$_1$–C$_4$-alkylthio, C$_1$–C$_4$-haloalkoxy, C$_1$–C$_4$-haloalkylthio, C$_1$–C$_4$-alkylsulfonyl, halogen, cyano, nitro, unsubstituted or substituted phenyl or unsubstituted or substituted phenoxy, m and p independently of one another are each 0, 1, 2 or 3 and n is 0 or 1, possess good fungicidal and herbicidal activity and are tolerated by plants.

Preferred compounds I are those in which the substituents have, for example, the following meanings: R$^1$ is hydrogen, C$_1$–C$_4$-alkyl, in particular methyl, ethyl or isopropyl, C$_2$–C$_4$-alkenyl, in particular allyl, or C$_2$–C$_4$-alkylcarbonyl, in particular acetyl, R is a straight-chain or branched, saturated or unsaturated C$_1$–C$_{10}$-hydrocarbon chain which is unsubstituted or substituted by halogen (fluorine, chlorine or bromine), in particular C$_1$–C$_6$-alkyl, especially methyl, ethyl, n-propyl, isopropyl, n-butyl, 1-methylpropyl, tert-butyl, n-pentyl, 3-methylbutyl, neopentyl or n-hexyl, in particular C$_3$–C$_5$-alkenyl, e.g. allyl, 3-methylallyl, 2-methylallyl, 3-butenyl or 3-methyl-2-butenyl, in particular C$_3$–C$_5$-alkynyl, e.g. propargyl, 2-butynyl, 3-methyl-3-buten-1-ynyl, 3-methyl-3-penten-1-ynyl, 2,3-dibromopropyl, 3-chloro-3-methylbutyl, 3-bromo-3-methylbutyl, 2,3-dibromo-3-methylbutyl or 3-trifluoromethyl-3-buten-1-ynyl, or the radical

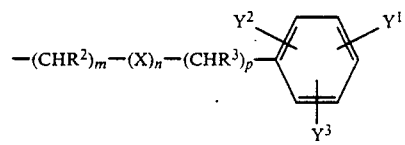

where Y$^1$, Y$^2$ and Y$^3$ are each hydrogen, C$_1$–C$_4$-alkyl, in particular 2-, 3- or 4-methyl or 4-tert-butyl, C$_1$–C$_4$-alkoxy, in particular 2-, 3- or 4-methoxy, C$_1$–C$_4$-haloalkyl, in particular 3- or 4-trifluoromethyl, C$_1$–C$_4$-alkylthio, in particular 4-methylthio, C$_1$–C$_4$-alkylsulfonyl, in particular 4-methylsulfonyl, halogen, in particular 3- or 4-fluoro, 2-, 3- or 4-chloro, 3-bromo, 2,4- or 3,4-dichloro, 2,4,5-trichloro or 2,4-dibromo, cyano, in particular 3- or 4-cyano, nitro, in particular 2-, 3- or 4-nitro, phenyl, C$_1$–C$_4$-alkylphenyl, halophenyl, phenoxy, C$_1$–C$_4$-alkylphenoxy or halophenoxy, and R is, in particular, phenyl, benzyl, 1-phenylethyl, phenoxymethyl, 1-phenoxyethyl, phenylthiomethyl, benzyloxy, 1-phenylethoxy, 3-(benzyloxy)propyl, 3-(1-phenylethoxy)propyl, 3-phenoxypropyl or 3-phenylthiopropyl.

We have also found that the novel, 2-substituted, 2,3-epoxy-5-cyclohexenone derivatives of the formula I can be prepared if a 2-substituted benzoquinone (Ann. Chem. 763 (1972), 135, Chem. Ber. 97 (1964), 1926 and Agr. Biol. Chem. 39 (1975), 555) of the formula II is subjected to a cycloaddition reaction with cyclopentadiene in roughly stoichiometric amounts in the presence or absence of a solvent to give a compound III (Chem. Ber. 90 (1960), 1896).

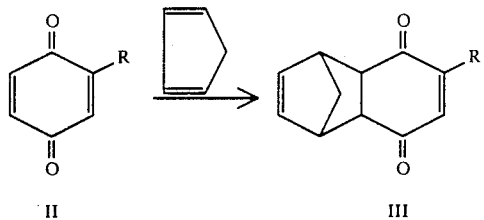

Suitable solvents are aromatic hydrocarbons, for example benzene, toluene, xylene, chlorohydrocarbons, e.g. methylene chloride, chloroform, carbon tetrachloride, 1,2-dichloroethane or 1,1,1-trichloroethane, ethers, e.g. diethyl ether, diisopropyl ether, methyl tert-butyl ether, tetrahydrofuran, dioxane or ethylene glycol ether, carboxylates, e.g. ethyl formate, ethyl acetate or ethyl propionate, ketones, e.g. acetone or methyl ethyl ketone, amides, e.g. formamide or dimethylformamide, and alcohols, e.g. methanol, ethanol, n- or isopropanol or n-, iso- or tertbutanol; methanol and ethanol are preferred. The reaction can be carried out at from −50° to 40° C., preferably from 0° to 20° C.

The compound III is converted to the compound IV by epoxidation (Houben-Weyl VI/3 page 397 et seq.).

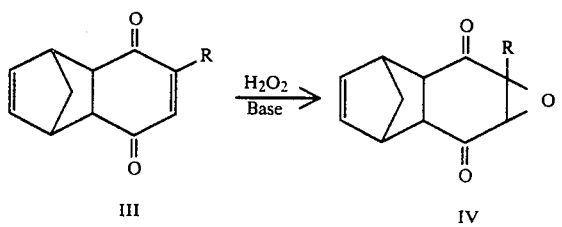

Examples of suitable peroxo compounds which, for example, can be used in stoichiometric amounts or in an excess of up to 20 times, are hydrogen peroxide, sodium perborate, sodium hypochlorite (NaOCl) and tert-butyl hydroperoxide. Suitable bases are alkali metal hydroxides, e.g. lithium hydroxide, sodium hydroxide or potassium hydroxide, alkali metal carbonates, e.g. sodium carbonate or potassium carbonate, organic ammonium hydroxides, e.g. benzyltrimethylammonium hydroxide, tetraethylammonium hydroxide or tetramethylammonium hydroxide, or a basic ion exchanger. In addition to water, alcohols, such as methanol, ethanol, n- or isopropanol or n-, iso- or tert-butanol, ethers, such as tetrahydrofuran, dioxane or ethylene glycol ether, or amides, such as formamide or dimethylformamide, are preferably used as solvents. Tetrahydrofuran is preferred. The reaction is carried out, for example, at from $-30°$ to $-50°$ C., preferably from $-10°$ to $+20°$ C.

The compound IV is subjected to thermolysis conditions (Chem. Ber. 90 (1960) 1896), Ia being formed.

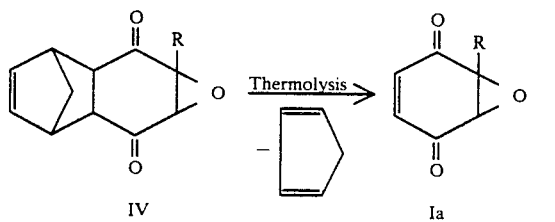

The compound IV is passed, for example at 150°–350° C. and under from 0.001 to 0.1 mmHg, briefly through an oven preheated at 300°–500° C., preferably 400°–450° C., and is pyrolysed.

The compound Ia is, if necessary, reduced to a compound Ib ($R^1$=H).

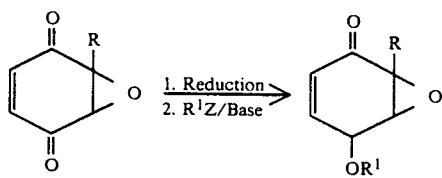

Suitable compounds for the reduction are hydride compounds, for example lithium borohydride, lithium cyanoborohydride, lithium trialkylborohydrides, sodium borohydride, sodium cyanoborohydride, sodium trialkylborohydrides, sodium trimethoxyborohydride, sodium triacetoxyborohydride, potassium borohydride, sodium trithiodihydridoboronate, tetralkylammonium borohydrides, tetraalkylammonium cyanoborohydrides, magnesium borohydride, calcium borohydride, zinc borohydride, diborane, bis(trifluoroacetoxy)borane, bis(triphenylphosphane)copper(I) borohydride, tetrakis(triphenylphosphane)dicopper(I) dicyanohexahydridoboronate, tetraalkyltin hydrides, sodium hydride and alkylsilicon hydrides. It is also possible to use metals, such as zinc or iron, in the presence of acids. Sodium cyanoborohydride is a preferred reducing agent.

Suitable solvents are hydrocarbons, e.g. petroleum ether, cyclohexane, naphtha, decalin, benzene, toluene or xylene, chlorohydrocarbons, e.g. methylene chloride, dichlorobutane, chloroform, carbon tetrachloride or 1,1,1-trichloroethane, ethers, e.g. diethyl ether, methyl tert-butyl ether, diisopropyl ether, ethylene glycol dimethyl ether, tetrahydrofuran or dioxane, amides, such as formamide, methylformamide or dimethylformamide, alcohols, such as methanol, ethanol, n- or isopropanol, n- or tert-butanol, and corresponding mixtures. Tetrahydrofuran and methanol are preferred. Because the compound Ia is unstable in the presence of bases, the reaction is carried out in a neutral to slightly acidic medium (pH 3–7) at from $-30°$ to $+40°$ C., preferably from $-10°$ to $+20°$ C., and is monitored by chromatography until starting material is no longer present. Acids which may be added to the generally alkaline reducing agents are dilute mineral acids, such as hydrochloric acid, sulfuric acid or phosphoric acid, as well as carboxylic acids, such as formic acid, acetic acid, propionic acid, trifluoroacetic acid, chloroacetic acid or oxalic acid, and buffer systems brought to an acidic pH. Acetic acid is preferred. For reactions in an aprotic medium it is possible to use Lewis acids, such as aluminum chloride, iron(III) chloride, zinc chloride or boron trifluoride etherate.

If necessary, the compound Ib ($R^1$=H) is converted to the compound Ib (where $R^1$ is not H).

The alkylation or acylation of the compound Ib can be carried out, in the presence of an acid acceptor, with an alkylation or acylating agent of the formula $R^1Z$, where Z is a group which can be readily eliminated, for example chloride, bromide, iodide, tosylate, mesylate, triflate or acetate. Preferably used acid acceptors are tertiary amines, alkaline earth metal compounds, ammonium compounds and alkali metal compounds, as well as mixtures of these. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, trisecbutylamine, tri-tert-butylamine, pyridine, α, β, γ-picoline, 2,6-lutidine, pyrimidine, N,N-dimethylaniline, N,N-diethylaniline, N-methylpyrrolidone and N-ethylpyrrolidone.

The reaction can be carried out in the presence or absence of a solvent at from 20° to 150° C. Suitable solvents are aromatic hydrocarbons, such as benzene, toluene, xylenes, chlorohydrocarbons, such as methylene chloride, chloroform, carbon tetrachloride, 1,2-dichloroethane, 1,1,1-trichloroethane or chlorobenzene, ethers, such as diethyl ether, diisopropyl ether, methyl tert-butyl ether, tetrahydrofuran, dioxane or ethylene glycol ether, ketones, such as acetone, methyl ethyl ketone or cyclohexanone, amides, such as formamide, methylformamide, dimethylformamide, N- methylpyrrolidone or N-ethylpyrrolidone, and nitriles, such as acetonitrile.

Compound no. 169 (2,3-epoxy-2-(3-methyl-3-butene-1-ynyl)-5-cyclohexen-4-ol-1-one=1-(3-methyl-3-buten-1-ynyl)-5-hydroxy-7-oxabicyclo[4.1.0]hept-3-en-2-one) can be prepared as described above. However, it can also be prepared by culturing of fungus DSM 3650 and separation from the culture filtrate.

Said fungus DSM 3650 was isolated from infested corn roots found in the Federal Republic of Germany (Krüger, W. and Speakman, J. B.; Zeitschrift für Pflanzenkrankheiten und Pflanzenschutz, 91 (1984) (1), 1-11).

A viable culture of this microorganism was deposited at the Deutsche Sammlung für Mikroorganismen (German Collection of Microorganisms), Griesebachstrasse 8, D-3400 Göttingen, and incorporated in its permanent collection. The microorganism is freely accessible to the public at this depository under its deposition number DSM 3650.

In general, compound no. 169 is prepared by culturing fungus DMS 3650 under aerobic conditions in a liquid medium containing assimilable sources or carbon, nitrogen and inorganic anions and cations, until a substantial amount of compound no. 169 has formed in the medium, and then isolating this compound from the medium.

Compound no. 169 is prepared, for example, by fermenting a liquid medium, which contains assimilable sources of carbon, nitrogen and inorganic anions and cations, under aerobic conditions, the medium being innoculated with a viable culture of fungus DSM 3650 or a mutant of this which produces compound no. 169, the organism being cultured for from 50 to 150 hours at from 20° to 30° C. and pH 5.5-8.0 with aeration under sterile conditions and with stirring, the culture filtrate being separated off and the compound being extracted from this.

Extraction of the compound no. 169 can be effected, for example, by extracting it from the culture filtrate with a water-immiscible solvent, or by freeze-drying the culture filtrate and then extracting the said compound from it with a solvent.

The extract can be purified, for example, by a chromatographic method.

Not only compound no. 169 as such but also the fermentation broth or total suspension of micro-organism DSM 3650 is suitable for use as a fungicide or herbicide.

The extract obtained from the fermentation broth or total suspension of microorganism DSM 3650 can also be used.

Compound no. 169 forms in the course of culturing fungus DSM 3650 under controlled conditions. General fermentation conditions Fungus DSM 3650 can be cultured in a wide variety of liquid culture media. Suitable nutrient media include an assimilable source of carbon, such as dextrin, sucrose, molasses, glycerol, etc.; an assimilable source of nitrogen, such as protein, protein hydrolysis products, polypeptides, amino acids, corn steep liquor, etc., and inorganic anions and cations, such as potassium, sodium, ammonium, calcium, sulfate, carbonate, phosphate, chloride, etc. Trace elements, such as boron, molybdenum, copper, manganese, zinc, iron, etc., are added to the media in the form of impurities in the other components of the media or as defined solutions. Aeration in bottles and tanks is carried out by passing sterile air through the nutrient medium or forcing such air onto the surface of the nutrient medium. Further movement in the tanks is ensured by means of a mechanical stirrer. If necessary, an antifoam, such as silicone oil, can be added.

EXAMPLE A

Preparation of Inoculum

Suitable media for culturing the inoculum are malt extract (2%) or sugar beet molasses (2%). aa) For fermentation on a small scale The nutrient media are sterilized. The agar (2% strength malt extract) present in a glass dish (9 cm diameter) and uniformly covered with the germ-free culture of fungus DSM 3650 is homogenized in a sterilized mixer with the addition of 200 ml of sterilized water (deionized) after which 40 ml portions of this homogenate are used as an inoculum for culturing the fungus in glass flasks (500 ml of nutrient medium in each case). ab) For fermentation on a large scale The nutrient media are sterilized. The agar (2% strength malt extract) contained in 5 glass dishes (diameter 9 cm) and uniformly covered with the germ-free culture of fungus DSM 3650 is homogenized in a sterilized mixer with the addition of 400 ml of sterilized water (deionized), after which half this homogenate in each case is transferred, as an inoculum, to 1 l glass flasks (each containing 500 ml of nutrient medium). The media are then shaken for 24-30 h at 25° C. on a rotary shaking machine at 130-150 rpm. This inoculum is then used to inoculate 50 l of a sterile sugar beet molasses medium (2%).

EXAMPLE B

Fermentation on a Small Scale

The fermentation media were prepared using sugar beet molasses (2%). The sterilized media (500 ml of nutrient medium per flask) were innoculated with the inoculum prepared according to Example aa and then shaken for from 5 to 6 days at 25° C. on a rotary shaking machine (130-150 rpm), after which the suspension was harvested.

EXAMPLE C

Fermentation on a Large Scale

The fermentation media were prepared using sugar beet molasses (2%). The sterilized medium (15 l of nutrient medium) were innoculated with the inoculum prepared according to Example ab, after which the fermentation is carried out at 25° C. and while stirring with a paddle stirrer operated at 150 rpm, a sterile air stream of from 1.5 to 2 l/min being maintained. Fermentation was carried out for from 5 to 8 days and the suspension was then harvested. Fermentations were carried out on a 50 l and 100 l scale similarly to this Example, the amount of inoculum and the sterile air stream being appropriately adapted to the changed volumes of nutrient medium.

EXAMPLE D

Isolation of Compound No. 169

A total volume of about 80 liters of suspension, prepared as described in Example b or c, was filtered and the mycelium cake was discarded. The culture filtrate thus obtained was extracted with dichloromethane in a continuous extraction process, and the solvent was then removed from this extract in a rotary evaporator under reduced pressure. The residue was taken up in a small volume of a 95:5 mixture of dichloromethane and dioxane and applied to a column equilibrated beforehand with the mobile phase, after which chromatography was carried out under pressure.

| Conditions: | | |
|---|---|---|
| Column: | Internal diameter | 5.4 cm |
| | Height of packing | 60.0 cm |
| Stationary phase: | Silica | 25–40 μm |
| | (MN Polygosil 60) | |
| Mobile phase: | 95:5 dichloromethane/ dioxane | |
| Flow rate: | 60 ml/min | |
| Pressure: | 1 bar | |

Detection of the eluate by photometer: λ = 245 nm

The fraction containing the major part of compound no. 169 was evaporated to dryness in a rotary evaporator under reduced pressure, the residue was then taken up in a little diisopropyl ether and the solution was applied to a chromatography column.

| Conditions: | | |
|---|---|---|
| Column: | Internal diameter | 2.0 cm |
| | Height of packing | 15.0 cm |
| Stationary phase: | Silica | 25–40 μm |
| | (MN Polygosil 60) | |
| Mobile phase: | Diisopropyl ether | |

The fraction containing the major part of compound no. 169 was evaporated to dryness in a rotary evaporator under reduced pressure and the residue was then taken up in from 20 to 50 ml of diisopropyl ether. The same volume of isooctane was added, and compound no. 169 crystallized out after some time. Recrystallization gave a very pure product.

PREPARATION EXAMPLES

1. Preparation of 2,3-epoxy-2-benzyl-5-cyclohexene-1,4-dione a) 19.9 g (0.1 mole) of 2-benzylbenzoquinone were suspended in 65 ml of ethanol, and 10 ml (0.11 mole) of cyclopentadiene were added at from 0° to 10° C., while stirring. The mixture was allowed to warm up to room temperature (20° C.) and stirred for a further hour, and the solvent was stripped off in a rotary evaporator. Recrystallization with ethanol gave 21.2 g (80%) of the adduct of type III (R=benzyl. Mp.: 77°–78° C.).

b) An ice-cold solution of 17.4 g of potassium carbonate in 200 ml of water and 62.2 ml of 30% strength hydrogen peroxide were added dropwise to 19.8 g (0.075 mole) of adduct III in 470 ml of tetrahydrofuran (THF) while cooling with ice. Thereafter, the mixture was warmed up to room temperature and stirred for a further 30 minutes. Water and methylene chloride were added, the aqueous phase was extracted twice with methylene chloride, and the combined organic phases were washed with water and dried. The solvent was removed and the crude product was then recrystallized from diethyl ether. 20.0 g (95%) of type IV were obtained. Mp.: 98°–99° C.

c) 6 g (0.021 mole) of the compound of type IV were premelted in a metal bath and then vaporized, and the vapor was pyrolysed at about 250°–270° C./0.01 mmHg in a quartz tube preheated to 420° C. and filled with Raschig rings. The crude product was condensed in a cold trap cooled with ice/water, and the cyclopentadiene was collected in a second downstream cold trap cooled with dry ice. Column chromatography using 1:9 ethyl acetate/pentane as the mobile phase gave 4.3 g (94%) of a yellow oil (Example no. 49). IR 1691 (C=O).

2. Preparation of 2,3-epoxy-2-benzyl-5-cyclohexen-4-ol-1-one

Sodium cyanoborohydride was added a little at a time to 2.5 g (0.0117 mole) of the compound of Example no. 49 in 50 ml of methanol and 5 ml of glacial acetic acid until starting material was just no longer detectable, the addition being monitored by thin layer chromatography. During the reaction, the apparatus was flushed with nitrogen. The major part of the methanol was stripped off, and the residue was introduced into water and extracted with methylene chloride. The organic phase was washed with water and dried. The solvent was removed and the crude product was then filtered rapidly over silica gel using 1:9 ethyl acetate/pentane as the mobile phase. 2.25 g (89%) of a yellowish oil (Example no. 189) were obtained. IR: 3410 (OH), 1675 (C=O).

The compounds below can be prepared in a similar manner.

TABLE 1

| Ex. No. | W | R | Physical data | | |
|---|---|---|---|---|---|
| | | | m.p. (°C.) | IR (cm$^{-1}$) | 1H-NMR (ppm) |
| 1 | C = O | CH$_3$ | 66–67 | | |
| 2 | C = O | CH$_2$CH$_3$ | | | |
| 3 | C = O | CH$_2$CH$_2$CH$_3$ | | | |
| 4 | C = O | CH(CH$_3$)$_2$ | | | |
| 5 | C = O | CH$_2$CH$_2$CH$_2$CH$_3$ | | | 3.90 (s,1H,C-H) |
| 6 | C = O | CH$^2$CH(CH$_3$)$_2$ | | | |
| 7 | C = O | CH(CH$_3$)CH$_2$CH$_3$ | | | |
| 8 | C = O | C(CH$_3$)$_3$ | 71–73 | | |
| 9 | C = O | CH$_2$CH$_2$CH$_2$CH$_2$CH$_3$ | | | |
| 10 | C = O | CH$_2$CH$_2$CH(CH$_3$)$_2$ | | | |
| 11 | C = O | CH$_2$C(CH$_3$)$_3$ | | | |
| 12 | C = O | CH$_2$CH$_2$CH$_2$CH$_2$CH$_2$CH$_3$ | | | |
| 13 | C = O | CH$_2$CH=CH$_2$ | | | |
| 14 | C = O | propargyl | | | |
| 15 | C = O | CH$_2$CH=CH—CH$_3$ | | | |
| 16 | C = O | CH$_2$—C(CH$_3$)=CH$_2$ | | | |
| 17 | C = O | CH$_2$—CH$_2$—CH=CH$_2$ | | | |
| 18 | C = O | 2-butynyl | | | |
| 19 | C = O | CH$_2$—CH=C((CH$_3$)$_2$ | | 1692 (C = O) | |
| 20 | C = O | 3-methyl-3-buten-1-ynyl | | 1700 (C = O) | |

TABLE 1-continued

| Ex. No. | W | R | m.p. (°C.) | IR (cm$^{-1}$) | 1H-NMR (ppm) |
|---|---|---|---|---|---|
| 21 | C=O | 3-methyl-3-penten-1-ynyl | | | |
| 22 | C=O | CH$_2$—CHBr—CH$_2$Br | | | |
| 23 | C=O | CH$_2$—CH$_2$—CCl(CH$_3$)$_2$ | | | |
| 24 | C=O | CH$_2$—CH$_2$—CBr(CH$_3$)$_2$ | | | |
| 25 | C=O | CH$_2$—CHBr—CBr(CH$_3$)$_2$ | | | |
| 26 | C=O | 3-trifluoromethyl-3-buten-1-ynyl | | | |

TABLE 2

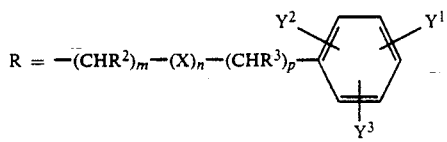

$$R = -(CHR^2)_m-(X)_n-(CHR^3)_p-\text{phenyl}(Y^1, Y^2, Y^3)$$

| Ex. No. | W | R$^2$ | R$^3$ | X | m | n | p | Y$^1$Y$^2$Y$^3$ | m.p. (°C.) | IR (cm$^{-1}$) | 1H-NMR (ppm) |
|---|---|---|---|---|---|---|---|---|---|---|---|
| 27 | C=O | — | — | — | 0 | 0 | 0 | H | | | |
| 28 | C=O | — | — | — | 0 | 0 | 0 | 3-F | | | |
| 29 | C=O | — | — | — | 0 | 0 | 0 | 4-F | | | |
| 30 | C=O | — | — | — | 0 | 0 | 0 | 2-Cl | 85–87 | | |
| 31 | C=O | — | — | — | 0 | 0 | 0 | 3-Cl | | | |
| 32 | C=O | — | — | — | 0 | 0 | 0 | 4-Cl | | | |
| 33 | C=O | — | — | — | 0 | 0 | 0 | 4-Br | | | |
| 34 | C=O | — | — | — | 0 | 0 | 0 | 3-CH$_3$ | | | |
| 35 | C=O | — | — | — | 0 | 0 | 0 | 4-CH$_3$ | | | |
| 36 | C=O | — | — | — | 0 | 0 | 0 | 4-t-C$_4$H$_9$ | | | |
| 37 | C=O | — | — | — | 0 | 0 | 0 | 3-CF$_3$ | | | |
| 38 | C=O | — | — | — | 0 | 0 | 0 | 4-CF$_3$ | | | |
| 39 | C=O | — | — | — | 0 | 0 | 0 | 3-OCH$_3$ | | | |
| 40 | C=O | — | — | — | 0 | 0 | 0 | 4-OCH$_3$ | | | |
| 41 | C=O | — | — | — | 0 | 0 | 0 | 4-SCH$_3$ | | | |
| 42 | C=O | — | — | — | 0 | 0 | 0 | 4-NO$_2$ | | | |
| 43 | C=O | — | — | — | 0 | 0 | 0 | 4-CN | | | |
| 44 | C=O | — | — | — | 0 | 0 | 0 | 4-Ph | | | |
| 45 | C=O | — | — | — | 0 | 0 | 0 | 4-OPh | | | |
| 46 | C=O | — | — | — | 0 | 0 | 0 | 2,4-Cl$_2$ | 119–120 | | |
| 47 | C=O | — | — | — | 0 | 0 | 0 | 2,4-Br$_2$ | | | |
| 48 | C=O | — | — | — | 0 | 0 | 0 | 2,4,5-Cl$_3$ | | | |
| 49 | C=O | H | — | — | 1 | 0 | 0 | H | | 1691 (C=O) | |
| 50 | C=O | H | — | — | 1 | 0 | 0 | 3-F | | | |
| 51 | C=O | H | — | — | 1 | 0 | 0 | 4-F | | | 3.30(s)2H; 3.65(d)1H; 6.74(m)2H; |
| 52 | C=O | H | — | — | 1 | 0 | 0 | 3-Cl | | | |
| 53 | C=O | H | — | — | 1 | 0 | 0 | 4-Cl | | | |
| 54 | C=O | H | — | — | 1 | 0 | 0 | 4-t-C$_4$H$_9$ | | | |
| 55 | C=O | H | — | — | 1 | 0 | 0 | 3-CF$_3$ | | | |
| 56 | C=O | H | — | — | 1 | 0 | 0 | 4-CF$_3$ | | | |
| 57 | C=O | H | — | — | 1 | 0 | 0 | 3-OCH$_3$ | | | |
| 58 | C=O | H | — | — | 1 | 0 | 0 | 4-OCH$_3$ | | | |
| 59 | C=O | H | — | — | 1 | 0 | 0 | 3-CN | | | |
| 60 | C=O | H | — | — | 1 | 0 | 0 | 4-CN | | | |
| 61 | C=O | H | — | — | 1 | 0 | 0 | 3-NO | | | |
| 62 | C=O | H | — | — | 1 | 0 | 0 | 4-NO$_2$ | | | |
| 63 | C=O | CH$_3$ | — | — | 1 | 0 | 0 | H | | | |
| 64 | C=O | CH$_3$ | — | — | 1 | 0 | 0 | 2-Cl | | | |
| 65 | C=O | CH$_3$ | — | — | 1 | 0 | 0 | 4-Cl | | | |
| 66 | C=O | CH$_3$ | — | — | 1 | 0 | 0 | 2-OCH$_3$ | | | |
| 67 | C=O | CH$_3$ | — | — | 1 | 0 | 0 | 3-OCH$_3$ | | | |
| 68 | C=O | CH$_3$ | — | — | 1 | 0 | 0 | 4-OCH$_3$ | | | |
| 69 | C=O | CH$_3$ | — | — | 1 | 0 | 0 | 2-NO$_2$ | | | |
| 70 | C=O | CH$_3$ | — | — | 1 | 0 | 0 | 4-NO$_2$ | | | |
| 71 | C=O | H | — | O | 1 | 1 | 0 | H | 125–125.5 | | |
| 72 | C=O | H | — | O | 1 | 1 | 0 | 3-F | | | |
| 73 | C=O | H | — | O | 1 | 1 | 0 | 4-F | | | |
| 74 | C=O | H | — | O | 1 | 1 | 0 | 2-Cl | | | |
| 75 | C=O | H | — | O | 1 | 1 | 0 | 3-Cl | | | |
| 76 | C=O | H | — | O | 1 | 1 | 0 | 4-Cl | | | |
| 77 | C=O | H | — | O | 1 | 1 | 0 | 4-Br | | | |
| 78 | C=O | H | — | O | 1 | 1 | 0 | 2,4-Cl$_2$ | 127–129 | | |
| 79 | C=O | H | — | O | 1 | 1 | 0 | 3,4-Cl$_2$ | | | |
| 80 | C=O | H | — | O | 1 | 1 | 0 | 2,4,5-Cl$_3$ | | | |
| 81 | C=O | H | — | O | 1 | 1 | 0 | 4-t-C$_4$H$_9$ | | | |
| 82 | C=O | H | — | O | 1 | 1 | 0 | 4-Ph | | | |
| 83 | C=O | H | — | O | 1 | 1 | 0 | 4-OPh | | | |
| 84 | C=O | H | — | O | 1 | 1 | 0 | 2-OCH$_3$ | 83–85 | | |

TABLE 2-continued $$R = -(CHR^2)_m-(X)_n-(CHR^3)_p-\phantom{X}\text{(phenyl with } Y^1, Y^2, Y^3\text{)}$$

| Ex. No. | W | R² | R³ | X | m | n | p | Y¹Y²Y³ | m.p. (°C.) | IR (cm⁻¹) | 1H-NMR (ppm) |
|---|---|---|---|---|---|---|---|---|---|---|---|
| 85 | C=O | H | — | O | 1 | 1 | 0 | 3-OCH₃ | | | |
| 86 | C=O | H | — | O | 1 | 1 | 0 | 4-OCH₃ | | | |
| 87 | C=O | H | — | O | 1 | 1 | 0 | 4-CN | | | |
| 88 | C=O | H | — | O | 1 | 1 | 0 | 4-CN | | | |
| 89 | C=O | H | — | O | 1 | 1 | 0 | 2-NO₂ | | | |
| 90 | C=O | H | — | O | 1 | 1 | 0 | 3-NO₂ | | | |
| 91 | C=O | H | — | O | 1 | 1 | 0 | 3-CF₃ | | | |
| 92 | C=O | H | — | O | 1 | 1 | 0 | 4-CF₃ | | | |
| 93 | C=O | H | — | O | 1 | 1 | 0 | 4-SCH₃ | | | |
| 94 | C=O | H | — | O | 1 | 1 | 0 | 4-SO₂CH₃ | | | |
| 95 | C=O | CH₃ | — | O | 1 | 1 | 0 | H | | | |
| 96 | C=O | CH₃ | — | O | 1 | 1 | 0 | 4-F | | | |
| 97 | C=O | CH₃ | — | O | 1 | 1 | 0 | 4-Cl | | | |
| 98 | C=O | CH₃ | — | O | 1 | 1 | 0 | 2,4-Cl₂ | | | |
| 99 | C=O | CH₃ | — | O | 1 | 1 | 0 | 2,4,5-Cl₃ | | | |
| 100 | C=O | CH₃ | — | O | 1 | 1 | 0 | 4-t-C₄H₉ | | | |
| 101 | C=O | CH₃ | — | O | 1 | 1 | 0 | 4-OCH₃ | | | |
| 102 | C=O | CH₃ | — | O | 1 | 1 | 0 | 4-CF₃ | | | |
| 103 | C=O | CH₃ | — | O | 1 | 1 | 0 | 4-CN | | | |
| 104 | C=O | CH₃ | — | O | 1 | 1 | 0 | 4-NO₂ | | | |
| 105 | C=O | CH₃ | — | O | 1 | 1 | 0 | 4-O-(C₆H₄)-CH₃ | | | |
| 106 | C=O | H | — | S | 1 | 1 | 0 | H | | | |
| 107 | C=O | H | — | S | 1 | 1 | 0 | 4-Cl | | | |
| 108 | C=O | — | H | O | 0 | 1 | 1 | H | | | |
| 109 | C=O | — | H | O | 0 | 1 | 1 | 3-F | | | |
| 110 | C=O | — | H | O | 0 | 1 | 1 | 4-F | | | |
| 111 | C=O | — | H | O | 0 | 1 | 1 | 3-Cl | | | |
| 112 | C=O | — | H | O | 0 | 1 | 1 | 4-Cl | | | |
| 113 | C=O | — | H | O | 0 | 1 | 1 | 4-Br | | | |
| 114 | C=O | — | H | O | 0 | 1 | 1 | 2-CH₃ | | | |
| 115 | C=O | — | H | O | 0 | 1 | 1 | 3-CH₃ | | | |
| 116 | C=O | — | H | O | 0 | 1 | 1 | 4-CH₃ | | | |
| 117 | C=O | — | H | O | 0 | 1 | 1 | 4-t-C₄H₉ | | | |
| 118 | C=O | — | H | O | 0 | 1 | 1 | 4-CF₃ | | | |
| 119 | C=O | — | H | O | 0 | 1 | 1 | 2,4-Cl₂ | | | |
| 120 | C=O | — | H | O | 0 | 1 | 1 | 3-CN | | | |
| 121 | C=O | — | H | O | 0 | 1 | 1 | 4-CN | | | |
| 122 | C=O | — | H | O | 0 | 1 | 1 | 4-NO₂ | | | |
| 123 | C=O | — | CH₃ | O | 0 | 1 | 1 | H | | | |
| 124 | C=O | — | CH₃ | O | 0 | 1 | 1 | 2,5-(CH₃)₂ | | | |
| 125 | C=O | H | H | O | 3 | 1 | 1 | H | | | |
| 126 | C=O | H | H | O | 3 | 1 | 1 | 4-F | | | |
| 127 | C=O | H | H | O | 3 | 1 | 1 | 4-Cl | | | |
| 128 | C=O | H | H | O | 3 | 1 | 1 | 4-CH₃ | | | |
| 129 | C=O | H | H | O | 3 | 1 | 1 | 4-CF₃ | | | |
| 130 | C=O | H | H | O | 3 | 1 | 1 | 4-CN | | | |
| 131 | C=O | H | H | O | 3 | 1 | 1 | 4-NO₂ | | | |
| 132 | C=O | H | CH₃ | O | 3 | 1 | 1 | H | | | |
| 133 | C=O | H | CH₃ | O | 3 | 1 | 1 | 2,5-(CH₃)₂ | | | |
| 134 | C=O | H | — | O | 3 | 1 | 0 | H | | | |
| 135 | C=O | H | — | O | 3 | 1 | 0 | 4-F | | | |
| 136 | C=O | H | — | O | 3 | 1 | 0 | 4-Cl | | | |
| 137 | C=O | H | — | O | 3 | 1 | 0 | 3-CH₃ | | | |
| 138 | C=O | H | — | O | 3 | 1 | 0 | 4-CH₃ | | | |
| 139 | C=O | H | — | O | 3 | 1 | 0 | 4-CF₃ | | | |
| 140 | C=O | H | — | S | 3 | 1 | 0 | H | | | |
| 141 | C=O | H | — | S | 3 | 1 | 0 | 4-F | | | |
| 142 | C=O | H | — | S | 3 | 1 | 0 | 4-Cl | | | |
| 143 | C=O | H | — | S | 3 | 1 | 0 | 3-CH₃ | | | |
| 144 | C=O | H | — | S | 3 | 1 | 0 | 4-CH₃ | | | |
| 145 | C=O | H | — | S | 3 | 1 | 0 | 4-CF₃ | | | |

TABLE 3

| Ex. no. | W | R¹ | R | m.p. (°C.) | IR (cm⁻¹) | 1H-NMR (ppm) |
|---|---|---|---|---|---|---|
| 146 | CHOR¹ | H | $CH_3$ | | | |
| 147 | CHOR¹ | $COCH_3$ | $CH_3$ | | | |
| 148 | CHOR¹ | $CH_3$ | $CH_3$ | | | |
| 149 | CHOR¹ | $CH_2-CH=CH_2$ | $CH_3$ | | | |
| 150 | CHOR¹ | H | n-$CH_2-CH_2CH_3$ | | | |
| 151 | CHOR¹ | $COCH_3$ | n-$CH_2-CH_2CH_3$ | | | |
| 152 | CHOR¹ | $CH_3$ | n-$CH_2-CH_2CH_3$ | | | |
| 153 | CHOR¹ | H | $CH(CH_3)_2$ | | | |
| 154 | CHOR¹ | $COCH_3$ | $CH(CH_3)_2$ | | | |
| 155 | CHOR¹ | $CH_3$ | $CH(CH_3)_2$ | | | |
| 156 | CHOR¹ | H | $CH_2CH_2CH_2CH_3$ | | 1685 (C=O) 3415 (OH) | |
| 157 | CHOR¹ | $COCH_3$ | $CH_2CH_2CH_2CH_3$ | | | |
| 158 | CHOR¹ | $CH_3$ | $CH_2CH_2CH_2CH_3$ | | | |
| 159 | CHOR¹ | $CH(CH_3)_2$ | $CH_2CH_2CH_2CH_3$ | | | |
| 160 | CHOR¹ | $CH_2-CH=CH_2$ | $CH_2CH_2CH_2CH_3$ | | | |
| 161 | CHOR¹ | H | $C(CH_3)_3$ | | | 3.81(m, 1H, C—H) 4.62(m, 1H, C—H) |
| 162 | CHOR¹ | $COCH_3$ | $C(CH_3)_3$ | | | |
| 163 | CHOR¹ | H | $CH_2CH=CHCH_3$ | | | |
| 164 | CHOR¹ | $COCH_3$ | $CH_2CH=CHCH_3$ | | | |
| 165 | CHOR¹ | $CH_3$ | $CH_2CH=CHCH_3$ | | | |
| 166 | CHOR¹ | H | $CH_2-CH=C(CH_3)_2$ | | | 3.64(m, 1H, C—H) 5.04(m, 1H, C—H) |
| 167 | CHOR¹ | $COCH_3$ | $CH_2-CH=C(CH_3)_2$ | | | |
| 168 | CHOR¹ | $CH_3$ | $CH_2-CH=C(CH_3)_2$ | | | |
| 169 | CHOR¹ | H | $-C\equiv C-\underset{\underset{CH_3}{\mid}}{C}=CH_2$ | | 1664, 2217, 3450 | 1.0(3H, s); 4.05(1H, s); 4.5(1H, m); 5.4–5.46(1H, d); 5.95–6.05(2H, m); 6.7–6.8 (1H, m) |

TABLE 4

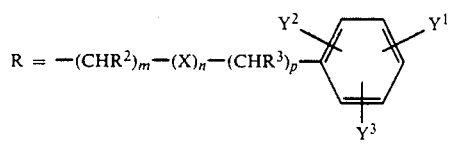

$$R = -(CHR^2)_m-(X)_n-(CHR^3)_p-\text{Ar}(Y^1, Y^2, Y^3)$$

| Ex. no. | W | R¹ | R² | R³ | X | m | n | p | Y¹Y²Y³ | m.p. (°C.) | IR (cm⁻¹) | 1H-NMR (ppm) |
|---|---|---|---|---|---|---|---|---|---|---|---|---|
| 170 | CHOR¹ | H | — | — | — | 0 | 0 | 0 | H | | | |
| 171 | CHOR¹ | $COCH_3$ | — | — | — | 0 | 0 | 0 | H | | | |
| 172 | CHOR¹ | $CH_3$ | — | — | — | 0 | 0 | 0 | H | | | |
| 173 | CHOR¹ | H | — | — | — | 0 | 0 | 0 | 4-F | | | |
| 174 | CHOR¹ | $COCH_3$ | — | — | — | 0 | 0 | 0 | 4-F | | | |
| 175 | CHOR¹ | H | — | — | — | 0 | 0 | 0 | 2-Cl | | | |
| 176 | CHOR¹ | $COCH_3$ | — | — | — | 0 | 0 | 0 | 2-Cl | | | |
| 177 | CHOR¹ | $CH_3$ | — | — | — | 0 | 0 | 0 | 2-Cl | | | |
| 178 | CHOR¹ | H | — | — | — | 0 | 0 | 0 | 4-Cl | | | |
| 179 | CHOR¹ | H | — | — | — | 0 | 0 | 0 | 3-$CH_3$ | | | |
| 180 | CHOR¹ | H | — | — | — | 0 | 0 | 0 | 4-$CH_3$ | | | |
| 181 | CHOR¹ | H | — | — | — | 0 | 0 | 0 | 4-t-$C_4H_9$ | | | |
| 182 | CHOR¹ | H | — | — | — | 0 | 0 | 0 | 3-$OCH_3$ | | | |
| 183 | CHOR¹ | H | — | — | — | 0 | 0 | 0 | 4-$OCH_3$ | | | |
| 184 | CHOR¹ | H | — | — | — | 0 | 0 | 0 | 4-Ph | | | |
| 185 | CHOR¹ | $COCH_3$ | — | — | — | 0 | 0 | 0 | 4-Ph | | | |
| 186 | CHOR¹ | H | — | — | — | 0 | 0 | 0 | 2,4-$Cl_2$ | | 3417 (OH) 1671 (C=O) | |
| 187 | CHOR¹ | $COCH_3$ | — | — | — | 0 | 0 | 0 | 2,4-$Cl_2$ | | | |
| 188 | CHOR¹ | $CH_3$ | — | — | — | 0 | 0 | 0 | 2,4-$Cl_2$ | | | |
| 189 | CHOR¹ | H | H | — | — | 1 | 0 | 0 | H | | 3410 (OH) 1675 (C=O) | |
| 190 | CHOR¹ | $COCH_3$ | H | — | — | 1 | 0 | 0 | H | | | |
| 191 | CHOR¹ | $CH_3$ | H | — | — | 1 | 0 | 0 | H | | | |
| 192 | CHOR¹ | H | H | — | — | 1 | 0 | 0 | H | | | |
| 193 | CHOR¹ | H | H | — | — | 1 | 0 | 0 | 3-F | | | |
| 194 | CHOR¹ | H | H | — | — | 1 | 0 | 0 | 4-F | | | |
| 195 | CHOR¹ | H | H | — | — | 1 | 0 | 0 | 3-Cl | | | |
| 196 | CHOR¹ | H | H | — | — | 1 | 0 | 0 | 4-Cl | | | |
| 197 | CHOR¹ | H | H | — | — | 1 | 0 | 0 | 4-t-$C_4H_9$ | | | |
| 198 | CHOR¹ | H | H | — | — | 1 | 0 | 0 | 4-$OCH_3$ | | | |
| 199 | CHOR¹ | H | $CH_3$ | — | — | 1 | 0 | 0 | H | | | |
| 200 | CHOR¹ | H | $CH_3$ | — | — | 1 | 0 | 0 | 2-Cl | | | |
| 201 | CHOR¹ | H | H | — | O | 1 | 1 | 0 | H | | 3436 (OH) 1686 (C=O) | |

TABLE 4-continued

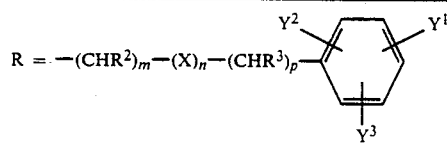

$$R = -(CHR^2)_m-(X)_n-(CHR^3)_p-$$

| Ex. no. | W | R¹ | R² | R³ | X | m | n | p | Y¹Y²Y³ | m.p. (°C.) | IR (cm⁻¹) | 1H-NMR (ppm) |
|---|---|---|---|---|---|---|---|---|---|---|---|---|
| 202 | CHOR¹ | COCH₃ | H | — | O | 1 | 1 | 0 | H | | | |
| 203 | CHOR¹ | CH₃ | H | — | O | 1 | 1 | 0 | H | | | |
| 204 | CHOR¹ | H | H | — | O | 1 | 1 | 0 | 3-F | | | |
| 205 | CHOR¹ | H | H | — | O | 1 | 1 | 0 | 4-F | | | |
| 206 | CHOR¹ | H | H | — | O | 1 | 1 | 0 | 3-Cl | | | |
| 207 | CHOR¹ | H | H | — | O | 1 | 1 | 0 | 4-Cl | | | |
| 208 | CHOR¹ | H | H | — | O | 1 | 1 | 0 | 2,4-Cl₂ | | | |
| 209 | CHOR¹ | COCH₃ | H | — | O | 1 | 1 | 0 | 2,4-Cl₂ | | | |
| 210 | CHOR¹ | H | CH₃ | — | O | 1 | 1 | 0 | H | | | |
| 211 | CHOR¹ | H | CH₃ | — | O | 1 | 1 | 0 | 2,4-Cl₂ | | | |
| 212 | CHOR¹ | H | H | — | S | 1 | 1 | 0 | H | | | |
| 213 | CHOR¹ | H | — | H | O | 0 | 1 | 1 | H | | | |
| 214 | CHOR¹ | H | — | H | O | 0 | 1 | 1 | 4-Cl | | | |
| 215 | CHOR¹ | H | — | H | O | 0 | 1 | 1 | 4-CH₃ | | | |
| 216 | CHOR¹ | H | — | CH₃ | O | 0 | 1 | 1 | H | | | |
| 217 | CHOR¹ | H | H | H | O | 3 | 1 | 1 | H | | | |
| 218 | CHOR¹ | H | H | H | O | 3 | 1 | 1 | 4-Cl | | | |
| 219 | CHOR¹ | H | H | H | O | 3 | 1 | 1 | 4-CH₃ | | | |
| 220 | CHOR¹ | H | H | CH₃ | O | 3 | 1 | 1 | H | | | |
| 221 | CHOR¹ | H | H | — | O | 3 | 1 | 0 | H | | | |
| 222 | CHOR¹ | H | H | — | O | 3 | 1 | 0 | 4-Cl | | | |
| 223 | CHOR¹ | H | H | — | O | 3 | 1 | 0 | 3-CH₃ | | | |
| 224 | CHOR¹ | H | H | — | S | 3 | 1 | 0 | H | | | |

In general terms, the novel compounds are extremely effective on a broad spectrum of phytopathogenic fungi, in particular those from the Phycomycetes class. Some of them have a systemic action and can be used as foliar and soil fungicides.

The fungicidal compounds are of particular interest for controlling a large number of fungi in various crops or their seeds, especially wheat, rye, barley, oats, rice, Indian corn, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Phytophthora infestans in tomatoes and potatoes,
Phytophthora parasitica in strawberries,
Pseudoperonospora cubensis in cucumbers,
Pseudoperonospora humuli in hops,
Peronospora destructor in onions,
Peronospora tabacina in tobacco,
Plasmopara viticola in grapes,
Plasmopara halstedii in sunflowers,
Sclerospora macrospora in Indian corn,
Bremia lactucae in lettuce,
Mucor mucedo in fruit,
Rhizopus nigricans in grapes and
Erysiphe graminis in cereals,
Uncinula necator in grapes,
Sphaerotheca fuliginea in roses,
Puccinia species in cereals,
Rhizoctonia species in cotton,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice and
Fusarium and Verticillium species in various plants.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, toluene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient.

The novel agents may also be used for protecting materials, for example against Paecilomyces variotii.

Some of the novel compounds have a very good action on human-pathogenic fungi, such as Trichophyton mentagrophytes and Candida albicans.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 71 is mixed with 10 parts by weight of N-methyl-alpha-pyrrolidone. A mixture is obtained which is suitable for application in the form of very fine drops.

II. 20 parts by weight of compound no. 189 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 201 is dissolved in a mixture consisting of 40 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 71 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 189 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 201 is intimately mixed with 97 parts by weight of particulate kaolin. A dust is obtained containing 3% by weight of the active ingredient.

VII. 30 parts by weight of compound no. 71 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 189 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 71 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers.

Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur, dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts, 2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ymethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, N-trichloromethylthiotetrahydrophthalimide (A) and 2-hydroxymethyl-2,3-epoxy-5-cyclohexene-1,4-dione (B) were used.

USE EXAMPLE 1

Action on Phytophthora infestans in tomatoes

Leaves of potted tomatoes of the "GroBe Fleischtomate" variety were sprayed with aqueous liquors containing (dry basis) 80 wt % of active ingredient and 20 wt % of emulsifier. 24 hours later, the leaves were infected with a zoospore suspension of the fungus Phytophthora infestans. The plants were then set up in a water vapor-saturated chamber at from 16° to 18° C. After 6 days, the disease had spread to such an extent on the untreated (infected) control plants that the fungicidal action of the compounds was able to be assessed.

The results of this experiment show that for example compounds nos. 71, 189 and 201, when applied as 0.025 wt % spray liquors, had a better fungicidal action (90%) than the prior art compounds A (70%) and B (10%).

USE EXAMPLE 2

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results of this experiment show that for example compound no. 71, applied as a 0.05% spray liquor, had a better fungicidal action (90%) than comparative agent B (60%).

USE EXAMPLE 3

Action on Rhizoctonia solani (watering treatment)

Steam-sterilized soil was inoculated with Rhizoctonia solani (the pathogen of stem canker) by admixing a maize meal/quartz sand mixture which was completely infested with Rhizoctonia solani mycelium. 1 g of this mixture was added to 1 kg of soil. Per dish, 20 cotton seeds of the "Stoneville" variety were sown in this soil. After six hours, the dish was watered with 50 ml of an aqueous suspension of the active ingredients, and then cultivated for 3 weeks in the greenhouse. The roots of all the plants were then checked for symptoms.

Evaluation: Statement of the number of healthy plants

The compound 1-(N-butylcarbamoyl)-2-(methoxycarboxamido)-benzimidazole (C) disclosed in U.S. Pat. No. 3,541,213 was used for comparison purposes.

TABLE

| Comp. no. | No. of healthy plants after treatment with aqueous formulations containing 0.05 and 0.0125% of the compounds | |
|---|---|---|
| | 0.05 | 0.0125 |
| C | 15 | 2 |
| 169 | 17 | 17 |
| Untreated control | 9 | 0 |

The strong fungitoxic action is readily apparent.

USE EXAMPLE 4

The action of compound no. 169 on the growth of crop and unwanted plants was demonstrated in greenhouse experiments.

The vessels employed were plastic flowerpots having a volume of 300 $cm^3$ and filled with a sandy loam containing about 3% humus. The seeds of the test plants were sown separately according to species. Certain species were grown separately in seed dishes before being transplanted to the experiment vessels a few days before treatment. Compound no. 169, dissolved in a solvent and emulsified in water as vehicle, was sprayed through finely distributing nozzles. The application rate was 2.0 kg of active ingredient per hectare.

The plants employed were Arachis hypogaea (groundnuts), Chenopodium album (lambsquarters), Euphorbia heterophylla (spurge), Medicago sativa (alfalfa), Mercurialis annua (mercury), Nicotinia rustica (tobacco), and Sinapis arvensis (yellow charlock).

The vessels were set up in the greenhouse—heat-loving species at from 20° to 35° C., and species from moderate climates at from 10° to 20° C. The experiment was run for 4 weeks. During this period the plants were tended and their reaction was assessed. The scale used for evaluation was 0 to 100, 0 denoting no damage or normal growth, and 100 denoting complete destruction of at least the visible plant parts.

Selective herbicidal action of compound no. 169 on postemergence treatment in the greenhouse

| Test plants | Damage in % after treatment with 2.0 kg/ha |
|---|---|
| Arachis hypogaea | 10 |
| Medicago sativa | 0 |
| Nicotinia rustica | 0 |
| Chenopodium album | 100 |
| Euphorbia heterophylla | 100 |
| Mercurialis annua | 95 |
| Sinapis arvensis | 93 |

At a rate of 2.0 kg/ha, compound no. 169 combated unwanted broadleaved plants. Certain broadleaved crop plants either suffered no damage or, at most, slight and acceptable temporary damage.

If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment). In view of its tolerance by crop plants and the great variety of application methods, and in view of the fungicidal action of compound no. 169, it may be used for protecting a large number of crop plants. The application rate may vary from 0.02 to 10.0 kg/ha and more, but is preferably from 0.05 to 3 kg/ha.

It may also be useful to apply the novel compounds in combination with other herbicides or in admixture with other fungicides and crop protection agents. The compounds may also be mixed with solutions of mineral salts used to remedy nutritional or trace element deficiencies. Surfactants and non-phytotoxic oils and oil concentrates may also be added to improve the action.

We claim:

1. A 2-substituted 2,3-epoxy-5-cyclohexenone derivative of formula I:

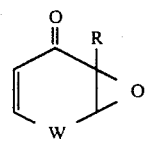

wherein W is C=O or CHOR$^1$, wherein R$^1$ is hydrogen, C$_{1-4}$-alkyl, C$_{2-4}$-alkenyl, C$_{2-4}$-alkynyl or C$_{2-4}$-alkylcarbonyl and R is an unsaturated hydrocarbon chain having from 3 to 5 carbon atoms, with the proviso that when W is carbonyl, R cannot be 3-methylbut-2-enyl.

2. The cyclohexenone derivative of claim 1, wherein said unsaturated chain having from 3 to 5 carbon atoms is a C$_{3-5}$-alkenyl selected from the group consisting of allyl, 3-methylallyl, 2-methylallyl, 3-butenyl and 3-methyl-2-butenyl or is C$_{3-5}$-alkynyl selected from the group consisting of propargyl, 2-butynyl and 3-methyl-3-buten-1-ynyl.

3. The cyclohexenone derivative of claim 1, wherein said C$_{1-4}$-alkyl group is methyl, ethyl or isopropyl and said C$_{2-4}$-alkenyl is allyl.

4. A fungicide containing an inert additive and an effective amount of a 2-substituted 2,3-epoxy-5-cyclohexenone derivative of formula (I)

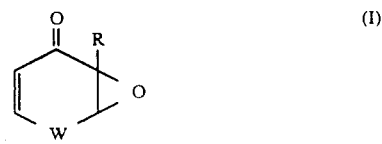

wherein W is C=O or CHOR$^1$, wherein R$^1$ is hydrogen, C$_{1-4}$-alkyl, C$_{2-4}$-alkenyl, C$_{2-4}$-alkynyl or C$_{2-4}$-alkylcarbonyl and R is an unsaturated hydrocarbon chain having from 3 to 5 carbon atoms, with the proviso that when W is carbonyl, R cannot be 3-methylbut-2-enyl.

5. The fungicide of claim 4, wherein said active cyclohexenone derivative constitutes from 0.1 to 95% by weight of the fungicide.

6. A herbicide containing an inert additive and an effective amount of a 2-substituted 2,3-epoxy-5-cyclohexenone derivative of formula (I)

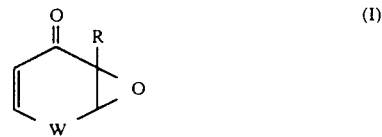

wherein W is C=O or CHOR$^1$, wherein R$^1$ is hydrogen, C$_{1-4}$-alkyl, C$_{2-4}$-alkenyl, C$_{2-4}$-alkynyl or C$_{2-4}$-alkylcarbonyl, and R is an unsaturated hydrocarbon chain having from 3° to 5° C. atoms, with the proviso that when W is carbonyl, R cannot be 3-methylbut-2-enyl.

7. 2,3-Epoxy-2-(3-methyl-3-buten-1-ynyl)-5-cyclohexen-4-ol-1-one.

* * * * *